US012131387B1

(12) United States Patent
Leners et al.

(10) Patent No.: US 12,131,387 B1
(45) Date of Patent: Oct. 29, 2024

(54) SYSTEMS AND METHODS OF AUTOMATICALLY CORRECTING ERRORS ASSOCIATED WITH PATIENT INSURANCE PROFILES

(71) Applicant: WALGREEN CO., Deerfield, IL (US)

(72) Inventors: Nicholas J. Leners, Round Lake, IL (US); Edward J. Bratton, Gurnee, IL (US)

(73) Assignee: WALGREEN CO., Deerfield, IL (US)

( * ) Notice: Subject to any disclaimer, the term of this patent is extended or adjusted under 35 U.S.C. 154(b) by 724 days.

(21) Appl. No.: 16/717,290

(22) Filed: Dec. 17, 2019

Related U.S. Application Data

(60) Provisional application No. 62/883,357, filed on Aug. 6, 2019.

(51) Int. Cl.
*G16H 10/60* (2018.01)
*G06F 16/23* (2019.01)
*G06F 40/40* (2020.01)
*G06Q 40/08* (2012.01)

(52) U.S. Cl.
CPC ......... *G06Q 40/08* (2013.01); *G06F 16/2379* (2019.01); *G06F 40/40* (2020.01); *G16H 10/60* (2018.01)

(58) Field of Classification Search
CPC .............................. G06Q 40/08; G16H 10/60
See application file for complete search history.

(56) References Cited

U.S. PATENT DOCUMENTS

| 5,628,530 | A | 5/1997 | Thornton |
| 5,832,449 | A | 11/1998 | Cunningham |
| 6,249,715 | B1 | 6/2001 | Yuri et al. |
| 6,529,892 | B1 | 3/2003 | Lambert |

(Continued)

OTHER PUBLICATIONS

Mekhjian et al., "Development of a Web-based Event Reporting System in an Academic Enviorment", Journal of the American Medical Informatics Association; Jan./Feb. 2004; 11, 1; pp. 11-18.

(Continued)

*Primary Examiner* — Mark Holcomb
(74) *Attorney, Agent, or Firm* — MARSHALL, GERSTEIN & BORUN LLP; Randall G. Rueth

(57) ABSTRACT

Systems and methods for automatically updating patient insurance information in response to a rejection by an insurance provider are provided. An indication that a prescription submitted to an insurance provider associated with a patient for payment has been rejected by the insurance provider may be received. The indication may include a rejection message associated with the rejection of the prescription. Based on the rejection message, the systems and methods may determine whether the rejection is related to incorrect insurance information. A likelihood that the prescription will be paid for when the insurance information is corrected may be calculated. Based on the calculated likelihood, the systems and methods may determine whether to initiate a patient insurance lookup system search. Corrected insurance information associated with the patient may be obtained using the patient insurance lookup system, and the prescription may be re-submitted for payment using the corrected insurance information for the patient.

14 Claims, 4 Drawing Sheets

(56) References Cited

U.S. PATENT DOCUMENTS

| | | | |
|---|---|---|---|
| 6,859,780 B1 | 2/2005 | Cunningham | |
| 6,978,286 B2 | 12/2005 | Francis et al. | |
| 6,993,402 B2 | 1/2006 | Klass et al. | |
| 7,014,063 B2 | 3/2006 | Shows et al. | |
| 7,020,697 B1 | 3/2006 | Goodman et al. | |
| 8,103,527 B1 | 1/2012 | Lasalle et al. | |
| 8,335,672 B1* | 12/2012 | Ringold | G06Q 10/10 703/2 |
| 8,347,295 B1 | 1/2013 | Robertson et al. | |
| 8,392,214 B1 | 3/2013 | Pinsonneault | |
| 8,489,415 B1 | 7/2013 | Ringold | |
| 8,781,854 B1 | 7/2014 | Harris, Sr. | |
| 11,282,611 B2* | 3/2022 | Ober, Jr. | G06F 40/211 |
| 2002/0143582 A1 | 10/2002 | Neuman et al. | |
| 2003/0074225 A1 | 4/2003 | Borsand et al. | |
| 2003/0125983 A1 | 7/2003 | Flack et al. | |
| 2003/0144884 A1 | 7/2003 | Mayaud | |
| 2003/0167190 A1 | 9/2003 | Rincavage et al. | |
| 2003/0225595 A1 | 12/2003 | Helmus et al. | |
| 2004/0059600 A1 | 3/2004 | Ball et al. | |
| 2004/0078247 A1 | 4/2004 | Rowe et al. | |
| 2004/0088187 A1 | 5/2004 | Chudy et al. | |
| 2004/0148195 A1 | 7/2004 | Kalies | |
| 2005/0033610 A1 | 2/2005 | Cunningham | |
| 2005/0060197 A1 | 3/2005 | Mayaud | |
| 2005/0071193 A1 | 3/2005 | Kalies | |
| 2005/0080651 A1 | 4/2005 | Morrison et al. | |
| 2005/0090425 A1 | 4/2005 | Reardan et al. | |
| 2005/0137912 A1 | 6/2005 | Rao et al. | |
| 2005/0154627 A1 | 7/2005 | Zuzek et al. | |
| 2006/0098193 A1 | 5/2006 | Rzasa et al. | |
| 2006/0161294 A1 | 7/2006 | DiMaggio | |
| 2007/0100662 A1 | 5/2007 | Suwalski et al. | |
| 2007/0214014 A1 | 9/2007 | Suwalski et al. | |
| 2008/0275723 A1 | 11/2008 | Wiley et al. | |
| 2009/0319311 A1 | 12/2009 | Mi et al. | |
| 2011/0029321 A1 | 2/2011 | Rourke et al. | |
| 2013/0246094 A1 | 9/2013 | Cruise | |
| 2014/0136231 A1 | 5/2014 | Suwalski et al. | |
| 2014/0278466 A1 | 9/2014 | Simmons et al. | |
| 2015/0154713 A1 | 6/2015 | Diaz et al. | |
| 2018/0089379 A1* | 3/2018 | Collins | G06Q 10/1057 |
| 2019/0095999 A1* | 3/2019 | Li | G06N 5/025 |
| 2020/0286616 A1* | 9/2020 | Dunn | G06N 3/08 |

OTHER PUBLICATIONS

The Institute for Safe Medication Practices. ISMP List of Error-Prone Abbreviations, Symbols, and Dose Designations and ISMP's list of high-alert medications. Accessed on Mar. 23, 2009 at http://web.archive/org/web/20050515210418/www.ismp.org/PDF?ErrorProne.pdf and http://web.archive.org/web20050315165646/www.ismp.org/MSarticles/highalert.

* cited by examiner

SYSTEMS AND METHODS OF AUTOMATICALLY CORRECTING ERRORS ASSOCIATED WITH PATIENT INSURANCE PROFILES

CROSS-REFERENCE TO RELATED APPLICATIONS

This application claims the priority benefit of U.S. Provisional Patent Application No. 62/883,357, filed on Aug. 6, 2019, entitled "Systems and Methods of Automatically Correcting Errors Associated with Patient Insurance Profiles;" and is related to commonly-owned U.S. patent application Ser. No. 16/408,784, filed on May 10, 2019, entitled "MODULAR PRESCRIPTION APPROVAL SYSTEM," which is a continuation of U.S. patent application Ser. No. 14/516,214, filed on Oct. 16, 2014, entitled "MODULAR PRESCRIPTION APPROVAL SYSTEM," the entire contents of each of which are herein expressly incorporated by reference.

FIELD OF THE DISCLOSURE

The present disclosure generally relates to obtaining or updating patient insurance information and, more particularly, to automatically updating patient insurance information in response to a rejection by an insurance provider.

BACKGROUND

The background description provided herein is for the purpose of generally presenting the context of the disclosure. Work of the presently named inventors, to the extent it is described in the background section, as well as aspects of the description that may not otherwise qualify as prior art at the time of filing, are neither expressly nor impliedly admitted as prior art against the present disclosure.

Pharmacies typically save patient insurance information in a file associated with the patient and may use this saved insurance information by default when the patient fills prescriptions at the pharmacy. However, in some instances, pharmacies need to contact patients to obtain or update the insurance information associated with the patient. For example, when a patient filling a prescription at a pharmacy provides his or her insurance card, sometimes the information on the card is out of date or otherwise incorrect. For instance, the patient may receive a new insurance card each year from an insurance provider, but may have provided a previous year's card at the pharmacy. Additionally, a patient may have changed insurance providers, but may have provided an insurance card from his or her previous insurance provider instead of the current insurance provider. Typically, the pharmacy does not learn that the patient's insurance information was incorrect until the pharmacy receives a rejection of the prescription from the insurance provider. Often, a pharmacy must contact the patient (typically via phone call) to obtain or update the patient's insurance information before the patient's prescription can be filled. However, contacting patients to obtain or update insurance information requires significant pharmacist time and resources, and may delay the patient's prescription fill.

In some examples, a pharmacy may have access to a patient insurance lookup service configured to search insurance records for various providers to obtain a patient's insurance information. However, searching for patients using a patient insurance lookup service can also be a drain on pharmacist time and resources. Moreover, patient insurance lookup services typically charge a fee for each search.

SUMMARY

In an embodiment, a computer-implemented method of automatically updating patient insurance information in response to a rejection by an insurance provider is provided. The computer-implemented method comprises: receiving, by a processor, an indication that a prescription submitted to an insurance provider associated with a patient for payment has been rejected by the insurance provider, wherein the indication includes a rejection message associated with the rejection of the prescription; determining, by a processor, based on the rejection message, that the rejection is related to incorrect insurance information associated with the patient; calculating, by a processor, a likelihood that the prescription will be paid for when the insurance information associated with the patient is corrected; determining, by a processor, based on the calculated likelihood that the prescription will be paid for when the insurance information associated with the patient is corrected, that a patient search using a patient insurance lookup system should be initiated; obtaining, by a processor, corrected insurance information associated with the patient from a patient search using the patient insurance lookup system; and submitting, by a processor, the prescription to the insurance provider or to an updated insurance provider for payment based on corrected insurance information associated with the patient obtained from the patient search using the patient insurance lookup system.

In another embodiment, a computer system for automatically updating patient insurance information in response to a rejection by an insurance provider is provided. The computer system comprises: one or more processors; and a non-transitory program memory communicatively coupled to the one or more processors and storing executable instructions. The executable instructions, when executed by the one or more processors, cause the computer system to: receive an indication that a prescription submitted to an insurance provider associated with a patient for payment has been rejected by the insurance provider, wherein the indication includes a rejection message associated with the rejection of the prescription; determine, based on the rejection message, that the rejection is related to incorrect insurance information associated with the patient; calculate a likelihood that the prescription will be paid for when the insurance information associated with the patient is corrected; determine, based on the calculated likelihood that the prescription will be paid for when the insurance information associated with the patient is corrected, that a patient search using a patient insurance lookup system should be initiated; obtain corrected insurance information associated with the patient from a patient search using the patient insurance lookup system; and submit the prescription to the insurance provider or to an updated insurance provider for payment based on corrected insurance information associated with the patient obtained from the patient search using the patient insurance lookup system.

In still another embodiment, a tangible, non-transitory computer-readable medium storing executable instructions for automatically updating patient insurance information in response to a rejection by an insurance provider is provided. The executable instructions, when executed by at least one processor of a computer system, cause the computer system to: receive an indication that a prescription submitted to an insurance provider associated with a patient for payment has been rejected by the insurance provider, wherein the indication includes a rejection message associated with the rejection of the prescription; determine, based on the rejection message, that the rejection is related to incorrect insurance information associated with the patient; calculate a likelihood that the prescription will be paid for when the insurance information associated with the patient is corrected; determine, based on the calculated likelihood that the prescription will be paid for when the insurance information associated with the patient is corrected, that a patient search using a patient insurance lookup system should be initiated; obtain corrected insurance information associated with the patient from a patient search using the patient insurance lookup system; and submit the prescription to the insurance provider or to an updated insurance provider for payment based on corrected insurance information associated with the patient obtained from the patient search using the patient insurance lookup system.

BRIEF DESCRIPTION OF THE DRAWINGS

The figures described below depict various aspects of the applications, methods, and systems disclosed herein. It should be understood that each figure depicts an embodiment of one or more particular aspects of the disclosed applications, systems and methods, and that each of the figures is intended to accord with one or more possible embodiments thereof. Furthermore, wherever possible, the following description refers to the reference numerals included in the following figures, in which features depicted in multiple figures are designated with consistent reference numerals.

DETAILED DESCRIPTION

Generally speaking, the systems and methods of the present application may be configured to automatically update patient insurance information in response to a rejection by an insurance provider. Insurer rejections may be analyzed to determine whether a patient insurance lookup search should be initiated, e.g., based on factors such as whether resolving the patient information will likely result in a resolution of the rejection, whether the medication would be covered by insurance, whether the amount that would be paid by the insurer would be worth the cost of the patient insurance lookup search, etc. In instances in which the patient insurance lookup search is initiated, patient information may be translated into a standard form to optimize the patient insurance lookup search. In some instances, patient insurance information obtained from the patient insurance lookup search may be adjusted as needed to meet the requirements of a particular plan determined to be associated with the patient. For example, some plans will not be processed by insurance providers unless a person code is added to the end of a recipient ID, while other plans do not have this requirement. Accordingly, in this example, the adjustment may include adding a person code to the end of the recipient ID for patients associated with certain plans before providing this information to an insurance provider for processing. Furthermore, patient insurance information obtained from the patient insurance lookup search may be added to a pharmacy database for future use.

Figure 1A:
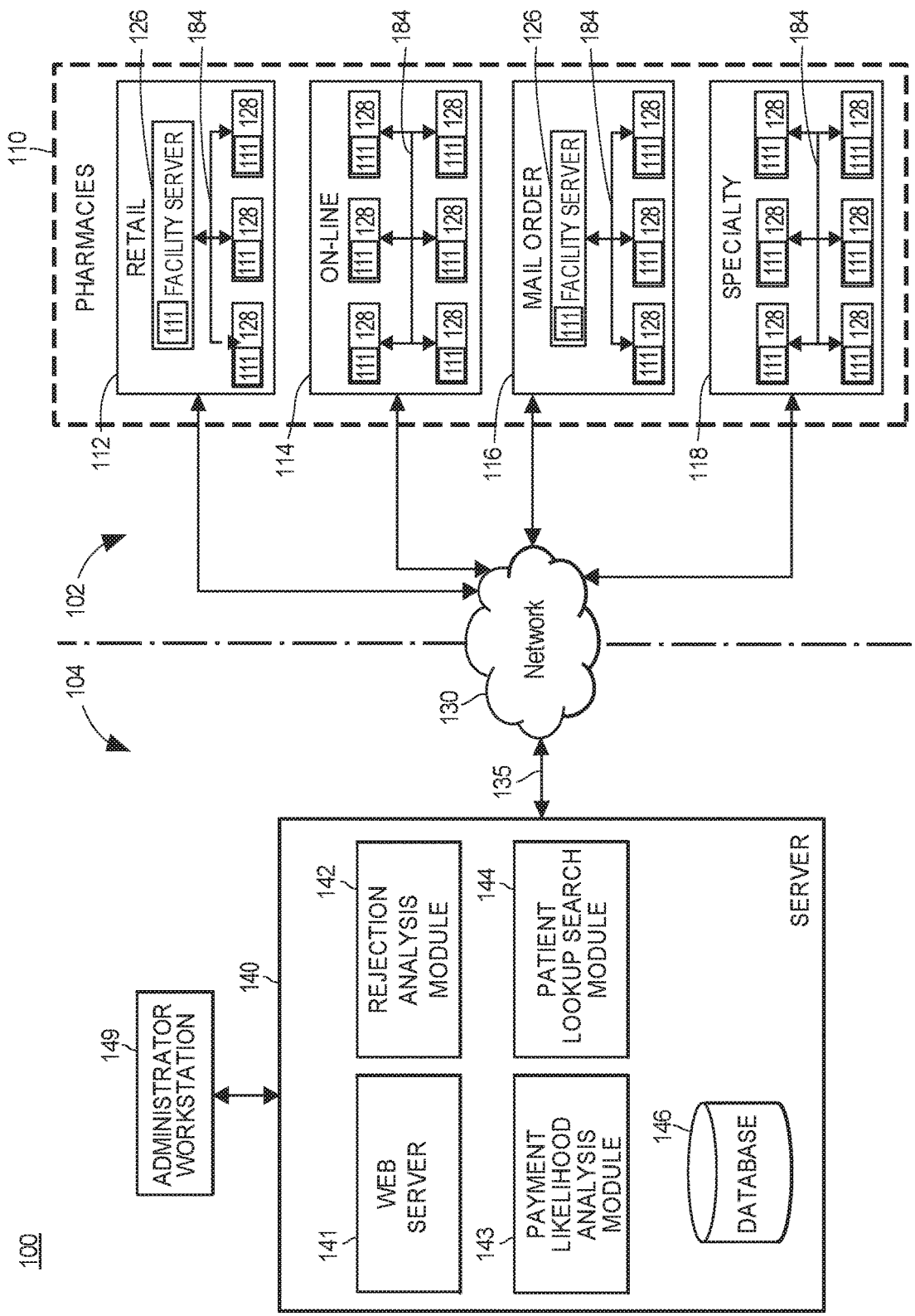
FIGS. 1A-1C illustrate block diagrams of a computer network, a computer server, and computing terminals on which an exemplary patient insurance correction system may operate to use pattern recognition techniques to analyze prescriber instructions in order to automatically update patient insurance information in response to a rejection by an insurance provider, in accordance with the embodiments described herein.

FIG. 1A illustrates a block diagram of an exemplary patient insurance correction system 100 for automatically updating patient insurance information in response to a rejection by an insurance provider, as described in greater detail with respect to FIG. 2 below. The high-level architecture includes both hardware and software applications, as well as various data communications channels for communicating data between the various hardware and software components. The patient insurance correction system 100 may be roughly divided into front-end components 102 and back-end components 104. The front-end components 102 may be disposed within one or more pharmacies 110. Where there is more than one pharmacy 110, the pharmacies 110 may be located, by way of example rather than limitation, in separate geographic locations from each other, including different areas of the same city or different states. The front-end components 102 may comprise a plurality of pharmacy workstations 128. The pharmacy workstations 128 may be local computers located in the various pharmacies 110 that execute a variety of applications related to pharmacy management. Pharmacists, technicians, or other users (not shown) may use the pharmacy workstations 128 to access patient information, enter new prescriptions, access insurance and payment information, and perform other pharmacy management-related tasks. Thus, the front-end components 102 may include pharmacy workstations 128 for servicing patients visiting an in-store retail pharmacy 112, pharmacy workstations 128 for servicing patients who choose to fill their prescriptions through an on-line pharmacy 114, a plurality of pharmacy workstations 128 for servicing patients who prefer to use the services of a mail-order pharmacy 116, and a plurality of pharmacy workstations 128 for servicing patients who require the services of a specialty pharmacy 118.

The front-end components 102 may also comprise a plurality of facility servers 126 disposed at the pharmacies 110, instead of or in addition to a plurality of pharmacy workstations 128. Each pharmacy 112, 114, 116, 118 may include one or more facility servers 126 that may be utilized to facilitate communications between the pharmacy workstations 128 and the back-end components 104 via a network 130, described below, and to store information for a plurality of patients, employees, accounts, or other records associated with each facility. Further, each pharmacy 112, 114, 116, 118 may include one or more pharmacy workstations 128 operatively connected to the facility server 126 via a local network 184.

The front-end components 102 may communicate with the back-end components 104 via the network 130. The network 130 may be a proprietary network, a secure public internet, a virtual private network or some other type of network, such as dedicated access lines, telephone lines, satellite links, cellular data networks, combinations of these, etc. Where the network 130 comprises the Internet, data communications may take place over the network 130 via an Internet communication protocol. The back-end components 104 include one or more servers 140. Each server 140 may include one or more computer processors adapted and configured to execute various software applications and components of the patient insurance correction system 100, in addition to other software applications. The server 140 may further include a database 146 that is adapted to store, inter alia, data related to correcting or updating patient insurance information. For instance, such data may include, e.g., insurance rejection codes related to issues involving incorrect patient insurance information, terms and/or phrases in insurance rejection messages related to issues involving incorrect patient insurance information, historical rejection messages associated with incorrect patient insurance information, listings of prescription medications that are unlikely to be covered by any insurance provider even when a patient's insurance information is fully updated, data indicative of outcomes of the pharmacy's previous requests for insurance payment for various medications, various threshold values, such as threshold percentages or threshold dollar amounts, pricing information for patient lookup searches, etc., to be used in methods for automatically updating patient insurance information in response to rejections by insurance providers, as discussed in greater detail with respect to FIG. 2. The server 140 may access data stored in the database 146, as well as data stored in other systems (not shown) when executing various functions and tasks associated with the operation of the patient insurance correction system 100.

Although the patient insurance correction system 100 is shown to include one server 140 and four pharmacies 112, 114, 116, and 118, it should be understood that different numbers may be utilized. For example, the system 100 may include a plurality of servers 140 and hundreds of pharmacies 110, all of which may be interconnected via the network 130. Furthermore, the database storage or processing performed by the one or more servers 140 may be distributed among a plurality of servers 140 in an arrangement known as "cloud computing." This configuration may provide various advantages, such as enabling near real-time uploads and downloads of information as well as periodic uploads and downloads of information. This may in turn support a thin-client embodiment of the pharmacy workstations 128, wherein most of the processing and storage is performed by the servers 140.

Figure 1B:
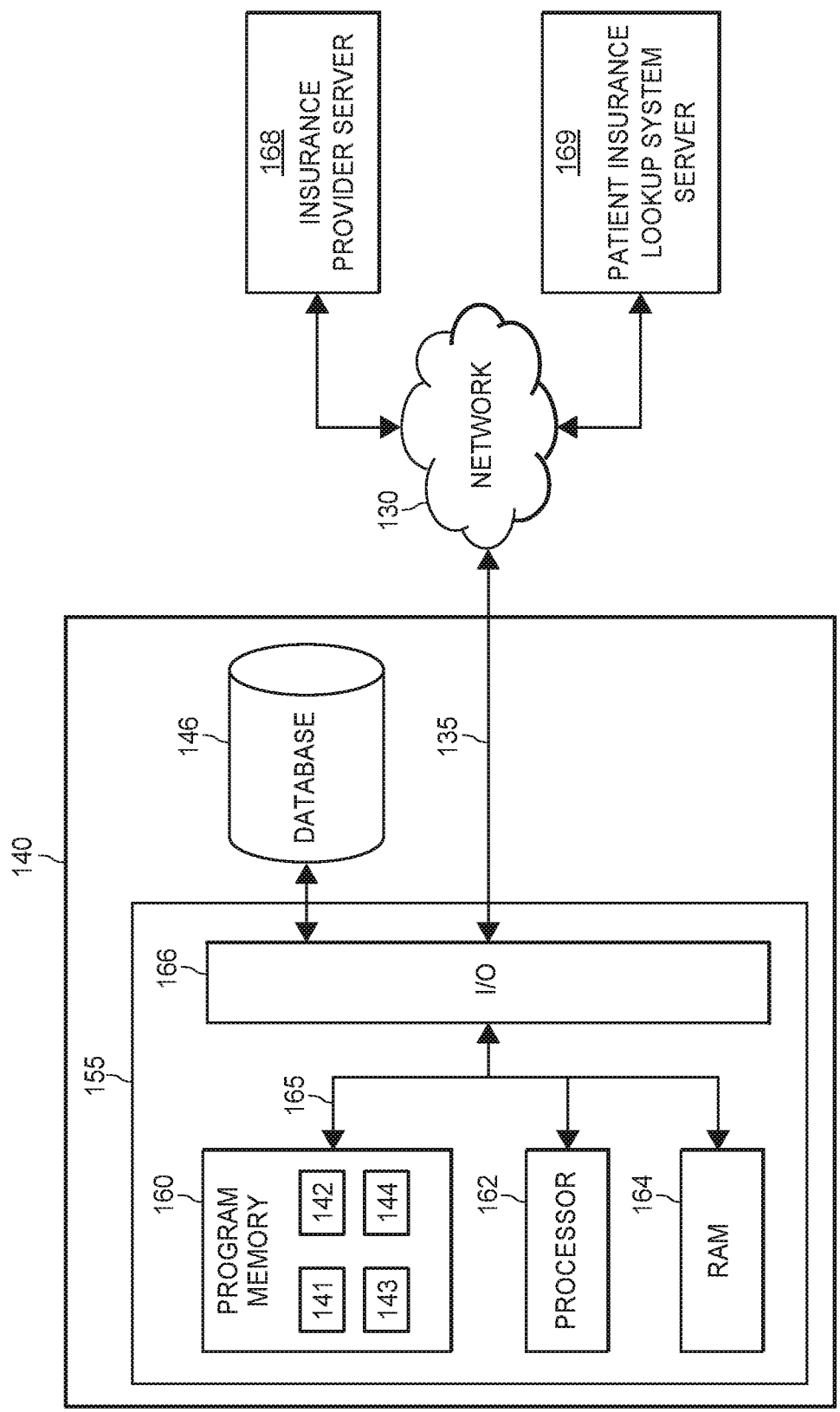

FIG. 1B is a schematic diagram of one possible embodiment of the server 140. The server 140 may have a controller 155 that is operatively connected to the database 146 via a link 156. It should be noted that, while not shown, additional databases may be linked to the controller 155 in a known manner. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one processor 162 is shown, the controller 155 may include multiple processors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135. In some examples, the server 140 may communicate with one or more insurance provider servers 168, e.g., via the network 130. For example, the server 140 may transmit prescriptions for payment by the insurance provider to an insurance provider server 168, and the insurance provider server 168 may transmit prescription approvals or rejections to the server 140. Additionally, in some examples, the server 140 may communicate with one or more patient insurance lookup system servers 169, e.g., via the network 130. For instance, the server 140 may transmit patient information (e.g., a patient's name, address, employer, etc.) to the patient insurance lookup system server 169 to initiate a patient search. Accordingly, the patient insurance lookup system server 169 may transmit search results to the server 140, and, in instances in which a fee is charged for using the patient insurance lookup system, the patient insurance lookup system server 169 may transmit data related to billing and/or payment to the server 140.

Figure 1C:
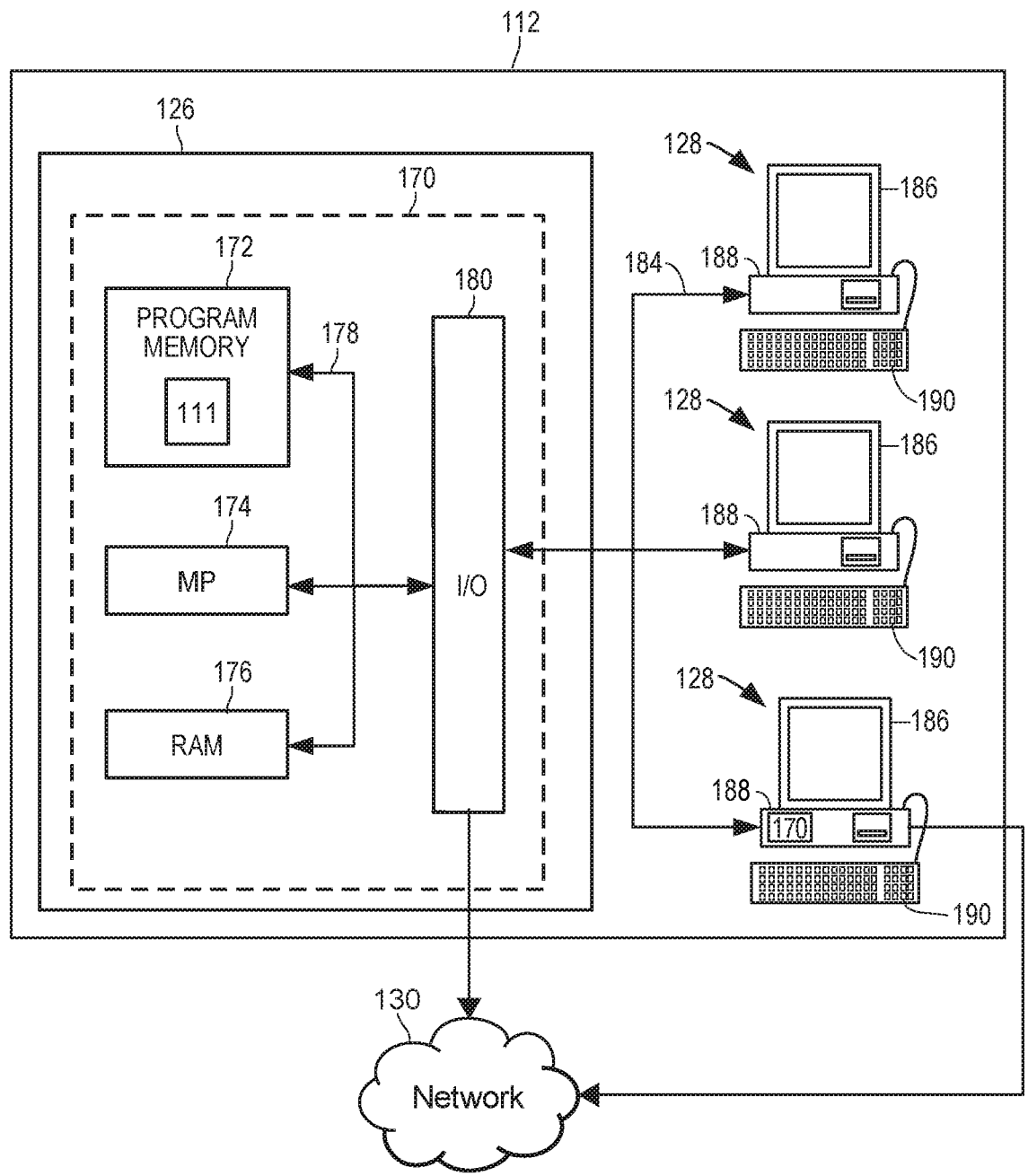

FIG. 1C is a schematic diagram of one possible embodiment of the front-end components 102 located in one or more of the pharmacies 110 from FIG. 1A, such as pharmacy 112. Although the following description addresses the design of the pharmacies 110, it should be understood that the design of one or more of the pharmacies 110 may be different than the design of other pharmacies 110. Also, each of the pharmacies 110 may have various different structures and methods of operation. It should also be understood that the embodiment shown in FIG. 1C illustrates some of the components and data connections present in an exemplary pharmacy 112, however it does not illustrate all of the data connections present in a typical pharmacy. For exemplary purposes, one design of a pharmacy is described below, but it should be understood that numerous other designs may be utilized.

Each pharmacy 110 may have one or more pharmacy workstations 128 or one or more facility servers 126. The facility server 126 may be operatively connected to a plurality of pharmacy workstations 128 via a network 184. The network 184 may be a wide area network (WAN), a local area network (LAN), or any other type of network readily known to those persons skilled in the art. The facility server 126 or workstations 128 may also be operatively connected to the server 140 via the network 130.

Each workstation 128 or facility server 126 includes a controller 170. Similar to the controller 155 from FIG. 1B, the controller 170 may include a program memory 172, a microcontroller or a microprocessor (MP) 174, a random-access memory (RAM) 176, and an input/output (I/O) circuit 180, all of which may be interconnected via an address/data bus 178. As discussed with reference to the controller 155, it should be appreciated that although only one microprocessor 174 is shown, the controller 170 may include multiple microprocessors 174. Similarly, the memory of the controller 170 may include multiple RAMs 176 and multiple program memories 172. Although the I/O circuit 180 is shown as a single block, the I/O circuit 180 may include a number of different types of I/O circuits. The RAM 176 and programs memories 172 may also be implemented as semiconductor memories, magnetically readable memories, and/or optically readable memories, for example. In some embodiments, the RAM 176 and program memories 172 may be combined into one memory without materially altering the system 100 as described herein.

The workstations 128 may further include displays 186 and keyboards 190, as well as a variety of other input/output devices (not shown) such as scanners, printers, touch screens, track pads, track balls, voice recognition systems, digital cameras, etc. Pharmacists, technicians, or other users may sign on to the pharmacy workstations 128 using any available technique, such as entering a user name and password. If users are required to sign on to the pharmacy workstations 128, this information may be passed via the network 184 to the facility server 126, so that the controller 170 will be able to identify which users are signed on to the system.

In one embodiment, the patient insurance correction system 100 may utilize a web interface to enable communication between the pharmacies 110 and the server 140, in which case the server 140 may include a web server 141. The web server 141 may be a stand-alone server, or a software module implemented within the server 140. The various front-end components 102 may include a web browser client application 111 to communicate with the back-end components 104. A web server 141 may transmit web pages to the facility servers 126 and pharmacy workstations 128 in response to URL requests received by the web server 141 from the front-end components 102 over the network 130. The web pages sent to the front-end components 102 may include data in the database 146. It should be noted that, while the current embodiment describes a web server 141 and a web browser client 111, each implementing the hyper-text transfer protocol, the web server 141 could implement any known or later-developed protocol compatible with the web browser client application 111 running on the front-end components 102 and adapted to the purpose of receiving and providing the necessary patient information via the network 130.

The server 140 may further include a number of software applications stored in a program memory 160. The software applications may be executed on the same computer processor as the web server application 141, or on different processors. The various software applications may include a rejection analysis module 142 configured to analyze a rejection code and/or rejection message received when a request for payment for a prescription is rejected by an insurance provider, e.g., in order to determine whether the rejection is related to incorrect insurance information associated with a patient (e.g., expired or otherwise outdated insurance information associated with the patient), as discussed in greater detail with respect to FIG. 2. Additionally, the various software applications may include a payment likelihood analysis module 142 configured to determine a likelihood that the rejected prescription would be paid for if insurance information for the patient were to be updated and/or corrected, as discussed in greater detail with respect to FIG. 2. Furthermore, the various software applications may include a patient lookup search module 144 configured to determine whether a patient lookup search should be initiated, to initiate the patient lookup search, and to obtain results from the patient lookup search (e.g., corrected and/or updated patient insurance information to be resubmitted with the prescription to an insurance provider for payment), as discussed in greater detail with respect to FIG. 2. Those of ordinary skill in the art will appreciate that these modules may be implemented in any number of modules; their functions need not be divided as indicated in FIG. 1A.

Finally, the back-end components 104 may include one or more administrator workstations 149. The administrator workstation 149 allows an authorized user to access the various applications running on the server 140 to alter or adjust the operation of the patient insurance correction system 100. For example, a regulatory agency may change its rules regarding the use of patient medical records. The administrator may then access the server 140 via the administrator workstation 149 and alter rules active in the modules 142-144 to reflect the changes in regulatory or interested third party rules.

For purposes of implementing the patient insurance correction system 100, the primary point of contact with the patient is through a pharmacy 110. The pharmacist filling the prescription will have access to one of the pharmacy workstations 128 and may invoke the patient insurance correction system 100 when he or she fills the patient's prescription. Alternatively, the patient insurance correction system 100 may be invoked automatically for each new prescription entered or by a broader system, such as a medication management system. In some embodiments, the patient insurance correction system 100 may be accessed by one or more additional computing devices (not shown) via the network 130.

Figure 2:
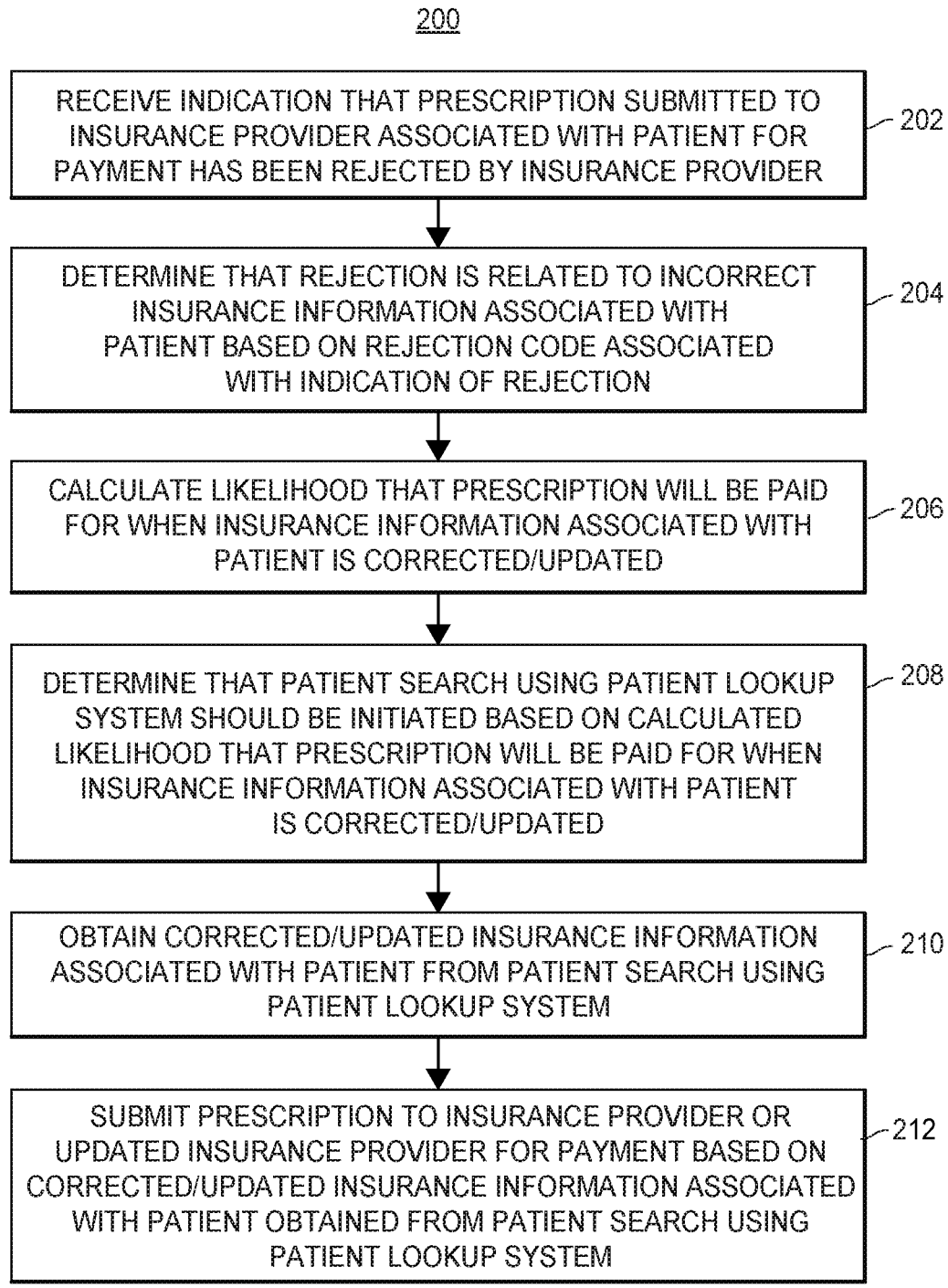
FIG. 2 illustrates a flow diagram of an exemplary method for automatically updating patient insurance information in response to a rejection by an insurance provider, in accordance with an embodiment of the present application.

Referring now to FIG. 2, a flow diagram of an exemplary method 200 for automatically updating patient insurance information in response to a rejection by an insurance provider is illustrated, in accordance with an embodiment of the present application. One or more steps of the method 200 may be implemented as a set of instructions stored on a computer-readable memory and executable on one or more processors.

In some examples, an indication that a prescription submitted to an insurance provider associated with a patient for payment has been rejected by the insurance provider may be received (block 202), e.g., by a processor associated with a pharmacy. For example, the indication may include a rejection message associated with the rejection of the prescription. In some examples, the indication may also include a rejection code associated with the rejection of the prescription. Based on the rejection message and/or the rejection code, a determination (block 204) may be made that the rejection is related to incorrect insurance information associated with the patient (e.g., expired or otherwise outdated insurance information associated with the patient). In other words, a determination may be made that the rejection is likely to be successfully resolved by correcting and/or updating insurance information associated with the patient. For example, certain rejection codes from some insurance providers only appear when insurance information associated with the patient is incorrect in some way, e.g., a code for "group number no longer valid," a code for "invalid group number," a code for "plan terminated," a code for "patient not found," etc.

However, in other instances, the code may be less clear, or may indicate a rejection for a reason not necessarily related to incorrect, expired, or outdated insurance information (e.g., a rejection related to the type of medication, a rejection related to the days' supply of the medication, etc.). In such instances, the rejection message (if included) may be analyzed to determine whether the rejection is related to incorrect, expired, or outdated insurance information associated with the patient and/or whether correcting or updating the patient's insurance information is likely to help resolve the rejection. For instance, the rejection message may be analyzed using natural language processing to identify an indication that the rejection is related to incorrect, expired, or outdated insurance information associated with the patient. For example, natural language processing may be used to identify words or phrases within the rejection message indicative of incorrect, outdated, or expired patient insurance information, or indicative of incorrect patient insurance information when combined with a particular rejection code. For instance, terms such as "plan," "group number," "not found," "invalid," "record," "expired," etc., in certain combinations may indicate that the message indicates that the insurance information submitted for the patient is incorrect, outdated, or expired. Moreover, in some examples, machine learning techniques may be used to identify common words or phrases found in historical rejection messages associated with incorrect patient insurance information. Accordingly, these words or phrases, when found in subsequent rejection messages, may indicate that the rejection is likely to be related to incorrect patient insurance information, and/or may indicate that the rejection is likely to be resolved by updating patient insurance information.

A likelihood that the prescription will be paid for when the insurance information associated with the patient is corrected and/or updated may be calculated (block 206). While in some examples this likelihood may be calculated for a prescription for which a request for payment has been rejected (as discussed with respect to block 202 and 204), in other examples, this likelihood may be calculated for a prescription for a patient for whom no insurance information is currently available, e.g., a new patient without insurance information on file in the first place.

The calculation of the likelihood that the prescription will be paid for when the insurance information associated with the patient is corrected and/or updated may be based on a likelihood that a medication associated with the prescription will be covered by insurance. That is, some prescription medications are unlikely to be covered by any insurance provider even when a patient's insurance information is fully updated. For instance, insurance providers typically do not pay for medications that are available over-the-counter (OTC), such as ibuprofen, acetaminophen, loratadine, etc. In some examples, the likelihood that a given medication will be covered may be calculated based on, e.g., analyzing outcomes of the pharmacy's previous requests for insurance payment for the medication. For instance, if only 20% of previous requests for insurance payment for the medication were successful, the likelihood that the medication will be covered may be a 20% likelihood.

In some examples, the calculated likelihood that the prescription will be paid for when the insurance information associated with the patient is corrected may include a calculated likelihood that greater than a threshold percentage of the cost (or greater than a threshold dollar amount) of the prescription will be paid for when the insurance information associated with the patient is corrected. For instance, insurance providers may be unlikely to pay more than a certain percentage of the cost of a certain medication, or may be unlikely to pay more than a certain dollar amount. The likelihood that an insurance provider will cover greater than a threshold percentage (or greater than a threshold dollar amount) of the cost of a given prescription may be calculated based on, e.g., analyzing outcomes of the pharmacy's previous requests for insurance payment for the medication. For instance, if insurance providers, on average, based on the pharmacy's records, will pay only 15% of the cost of a given medication, the likelihood that greater than a threshold percentage of 50% of the cost of the prescription will be paid for by any insurance provider will be low. Similarly, if insurance providers, on average, based on the pharmacy's records, will only pay $5 of the cost of a given medication, the likelihood that greater than a threshold $50 dollar amount of the cost of the prescription will be paid for by any insurance provider will be low.

Based on the calculated likelihood that the prescription will be paid for when the insurance information associated with the patient is corrected, a determination (block 208) may be made that a patient search using a patient insurance lookup system should be initiated. For instance, the patient lookup search may be initiated when the likelihood that the medication will be covered when the insurance information associated with the patient is corrected is greater than a threshold percentage (e.g., 50%, 70%, 90%), etc. As another example, the patient lookup search may be initiated when the likelihood that more than 50% (or some other threshold percentage) of the cost of the prescription will be covered when the insurance information associated with the patient is corrected is greater than a threshold percentage (e.g., 50%, 70%, 80%), etc. Moreover, as another example, the patient lookup search may be initiated when the likelihood that more than $50 (or some other dollar amount) of the cost of the prescription will be covered when the insurance information associated with the patient is corrected is greater than a threshold percentage (e.g., 50%, 70%, 80%), etc. In some examples, the determination may be made based on some combination or weighting of these various likelihood calculations.

Furthermore, in some examples, this determination may also be based on a cost associated with initiating a patient search. For example, the cost of initiating a patient search may be compared to the dollar amount of the cost of the prescription that the insurance provider is likely to cover when the patient's insurance information is corrected.

Once a determination has been made that the patient search using the patient insurance lookup system should be initiated, corrected insurance information associated with the patient may be obtained (block 210) using the patient insurance lookup system, e.g., by searching for an insurance match using the patient insurance lookup system based on the patient's name, address, or other information, e.g., from a pharmacy database such as database 146. In some examples, the patient's name, address, or other information may be standardized, abbreviated, or otherwise placed in a standard form associated with the patient insurance lookup system before the search is initiated in order to optimize the search. For instance, regular expressions may be used to replace, abbreviate, and/or re-organize the patient information to be used in patient insurance lookup system search.

The prescription may be submitted (block 212) to the insurance provider or to an updated insurance provider for payment based on the corrected or updated insurance information associated with the patient obtained using the patient insurance lookup system. Additionally, in some examples, the corrected insurance information associated with the patient obtained from the patient search using the patient insurance lookup system may be added to a database of the pharmacy associated with the patient.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computer-implemented method of automatically updating patient insurance information in response to a rejection by an insurance provider, comprising:
   receiving, by a processor, an indication that a prescription submitted to an insurance provider associated with a patient for payment has been rejected by the insurance provider, wherein the indication includes a rejection message associated with the rejection of the prescription;
   analyzing, by a processor, the rejection message using natural language processing to identify an indication that the rejection is related to incorrect insurance information associated with the patient;
   calculating, by a processor, a likelihood that the prescription will be paid for when the insurance information associated with the patient is corrected, wherein calculating the likelihood that the prescription will be paid for when the insurance information associated with the patient is corrected includes:
      determining, by a processor, an estimated dollar amount, of the cost of the prescription, that will be paid for when the insurance information associated with the patient is corrected;
   comparing, by a processor, the estimated dollar amount to a cost associated with initiating a patient search;
   initiating, by a processor, a patient search using a patient insurance lookup system when the likelihood is greater than a threshold likelihood, and based on comparing the estimated dollar amount, of the cost of the prescription, that will be paid for when the insurance information associated with the patient is corrected, to the cost associated with initiating the search, wherein the patient search includes:
      translating, by a processor, information associated with the patient into a standardized form associated with the patient insurance lookup system; and
      obtaining, by a processor, corrected insurance information associated with the patient from a patient search using the patient insurance lookup system based on the information associated with the patient as translated into the standardized form associated with the patient lookup system; and
   transmitting, by a processor, the prescription to a server associated with the insurance provider or to a server associated with an updated insurance provider for payment based on corrected insurance information associated with the patient obtained from the patient search using the patient insurance lookup system.

2. The computer-implemented method of claim 1, wherein the indication further includes a rejection code associated with the rejection of the prescription, and wherein determining that the rejection is related to incorrect insurance information associated with the patient is further based on the rejection code.

3. The computer-implemented method of claim 1, wherein calculating a likelihood that the prescription will be paid for when the insurance information associated with the patient is corrected is based on a likelihood that a medication associated with the prescription will be covered by insurance.

4. The computer-implemented method of claim 1, wherein the calculated likelihood that the prescription will be paid for when the insurance information associated with the patient is corrected includes a calculated likelihood that greater than a threshold percentage of the cost of the prescription will be paid for when the insurance information associated with the patient is corrected.

5. The computer-implemented method of claim 1, further comprising: adding the corrected insurance information associated with the patient obtained from the patient search using the patient insurance lookup system to a database of a pharmacy associated with the patient.

6. A computer system for automatically updating patient insurance information in response to a rejection by an insurance provider, comprising:
   one or more processors; and
   a non-transitory program memory communicatively coupled to the one or more processors and storing executable instructions that, when executed by the one or more processors, cause the computer system to:
   receive an indication that a prescription submitted to an insurance provider associated with a patient for payment has been rejected by the insurance provider, wherein the indication includes a rejection message associated with the rejection of the prescription;
   analyzing, by a processor, the rejection message using natural language processing to identify an indication that the rejection is related to incorrect insurance information associated with the patient;
   calculate a likelihood that the prescription will be paid for when the insurance information associated with the patient is corrected, wherein calculating the likelihood that the prescription will be paid for when the insurance information associated with the patient is corrected includes:
      determining an estimated dollar amount, of the cost of the prescription, that will be paid for when the insurance information associated with the patient is corrected;
   comparing the estimated dollar amount to a cost associated with initiating a patient search;
   initiate, a patient search using a patient insurance lookup system when the likelihood is greater than a threshold likelihood, and based on comparing the estimated dollar amount, of the cost of the prescription, that will be paid for when the insurance information associated with the patient is corrected, to the cost associated with initiating the search, wherein the patient search includes:
      translating information associated with the patient into a standardized form associated with the patient insurance lookup system; and
      obtaining corrected insurance information associated with the patient from a patient search using the patient insurance lookup system based on the information associated with the patient as translated into the standardized form associated with the patient lookup system; and
   transmit the prescription to a server associated with the insurance provider or to a server associated with an updated insurance provider for payment based on corrected insurance information associated with the patient obtained from the patient search using the patient insurance lookup system.

7. The computer system of claim 6, wherein the indication further includes a rejection code associated with the rejection of the prescription, and wherein determining that the rejection is related to incorrect insurance information associated with the patient is further based on the rejection code.

8. The computer system of claim 6, wherein the executable instructions cause the computer system to calculate a likelihood that the prescription will be paid for when the insurance information associated with the patient is corrected based on a likelihood that a medication associated with the prescription will be covered by insurance.

9. The computer system of claim 6, wherein the calculated likelihood that the prescription will be paid for when the insurance information associated with the patient is corrected includes a calculated likelihood that greater than a threshold percentage of the cost of the prescription will be paid for when the insurance information associated with the patient is corrected.

10. The computer system of claim 6, wherein the executable instructions further cause the computer system to add the corrected insurance information associated with the patient obtained from the patient search using the patient insurance lookup system to a database of a pharmacy associated with the patient.

11. A tangible, non-transitory computer-readable medium storing executable instructions for automatically updating patient insurance information in response to a rejection by an insurance provider that, when executed by at least one processor of a computer system, cause the computer system to:

receive an indication that a prescription submitted to an insurance provider associated with a patient for payment has been rejected by the insurance provider, wherein the indication includes a rejection message associated with the rejection of the prescription;

analyzing, by a processor, the rejection message using natural language processing to identify an indication that the rejection is related to incorrect insurance information associated with the patient;

calculate a likelihood that the prescription will be paid for when the insurance information associated with the patient is corrected, wherein calculating the likelihood that the prescription will be paid for when the insurance information associated with the patient is corrected includes:

determining an estimated dollar amount, of the cost of the prescription, that will be paid for when the insurance information associated with the patient is corrected;

comparing the estimated dollar amount to a cost associated with initiating a patient search;

initiate, a patient search using a patient insurance lookup system when the likelihood is greater than a threshold likelihood, and based on comparing the estimated dollar amount, of the cost of the prescription, that will be paid for when the insurance information associated with the patient is corrected, to the cost associated with initiating the search, wherein the patient search includes:

translating information associated with the patient into a standardized form associated with the patient insurance lookup system; and obtaining corrected insurance information associated with the patient from a patient search using the patient insurance lookup system based on the information associated with the patient as translated into the standardized form associated with the patient lookup system; and transmit the prescription to a server associated with the insurance provider or to a server associated with an updated insurance provider for payment based on corrected insurance information associated with the patient obtained from the patient search using the patient insurance lookup system.

12. The tangible, non-transitory computer-readable medium of claim 11, wherein the indication further includes a rejection code associated with the rejection of the prescription, and wherein determining that the rejection is related to incorrect insurance information associated with the patient is further based on the rejection code.

13. The tangible, non-transitory computer-readable medium of claim 11, wherein the executable instructions cause the computer system to calculate a likelihood that the prescription will be paid for when the insurance information associated with the patient is corrected based on a likelihood that a medication associated with the prescription will be covered by insurance.

14. The tangible, non-transitory computer-readable medium of claim 11, wherein the calculated likelihood that the prescription will be paid for when the insurance information associated with the patient is corrected includes a calculated likelihood that greater than a threshold percentage of the cost of the prescription will be paid for when the insurance information associated with the patient is corrected.

\* \* \* \* \*